United States Patent [19]

Lowrie et al.

[11] Patent Number: 5,032,584
[45] Date of Patent: * Jul. 16, 1991

[54] S-DIASTEREOMER OF AN N6-((2-HYDROXYPROPYL)ARYL)ADENOSINE AND ITS MEDICINAL USES

[75] Inventors: Harman S. Lowrie, Northbrook; Gerald M. Walsh, Lindenhurst, both of Ill.

[73] Assignee: G. D. Searle & Co., Chicago, Ill.

[*] Notice: The portion of the term of this patent subsequent to Jul. 9, 2008 has been disclaimed.

[21] Appl. No.: 262,864

[22] Filed: Oct. 26, 1988

[51] Int. Cl.$^5$ .................... A61K 31/70; C07H 19/167
[52] U.S. Cl. .................... 514/46; 514/45; 536/26; 536/24
[58] Field of Search .................... 514/46; 536/26

[56] References Cited

U.S. PATENT DOCUMENTS

| | | | |
|---|---|---|---|
| 3,502,649 | 3/1970 | Thiel et al. | 536/26 |
| 3,551,409 | 12/1970 | Kampe et al. | 536/26 |
| 3,590,029 | 6/1971 | Koch et al. | 536/26 |
| 3,851,056 | 11/1974 | Stork et al. | 536/26 |
| 3,929,763 | 12/1975 | Fauland et al. | 536/26 |
| 4,340,730 | 7/1982 | Henderson et al. | 536/26 |
| 4,388,308 | 6/1983 | Hamilton et al. | 536/26 |

FOREIGN PATENT DOCUMENTS

2007273 8/1971 Fed. Rep. of Germany .
8111332 12/1981 France .

OTHER PUBLICATIONS

Sollevi et al., Acta Physiol. Scand., 120, 171–176 (1984).
Kassell et al., J. Neurosurg., 58, 69076 (1983).

*Primary Examiner*—Johnnie R. Brown
*Assistant Examiner*—L. Eric Crane
*Attorney, Agent, or Firm*—Joy A. Serauskas; Paul D. Matukaitis

[57] ABSTRACT

A novel S diastereomer of an N6-[(2-hydroxypropyl)aryl] adenosine, which diastereomer exhibits fewer CNS side effects than the racemate, but with no decrease in cardiovascular activity. The invention further provides for compositions incorporating the diastereomer, and methods of its use, as well as pharmaceutically acceptable salts thereof.

6 Claims, No Drawings

S-DIASTEREOMER OF AN N6-((2-HYDROXYPROPYL)ARYL)ADENOSINE AND ITS MEDICINAL USES

BACKGROUND OF THE INVENTION

The present invention provides a novel compound, novel compositions, methods of their use and methods of their manufacture, such compound pharmacologically useful in the treatment of hypertension, congestive heart failure and angina in mammals. More specifically, the compound of the present invention is an orally active renin-release inhibitor (as opposed to a direct-acting renin-inhibiting compound) agent which, by effectively blocking plasma renin activity, thereby blocks the production of angiotensin II, which is a powerful vasoconstrictor. Since renin is involved in the pathogenesis of hypertension, congestive heart failure and angina in mammals, it can be seen that the novel compound of the present invention is useful in the treatment of these pathological disease states.

Hypertension is a disease characterized by increased vascular resistance, increased arterial blood pressure, and, in some cases, increased plasma renin activity. Renin may be involved in the pathogenesis of hypertension even if its level is not elevated in the plasma.

The renin-angiotensin system exists in every vertebrate class studied. The main source of renin is the kidney, from which it is secreted by the granular juxtaglomerular cells that lie in the walls of the afferent arterioles as they enter the glomeruli. These are endocrine cells in the sense that they discharge their secretory product, renin, directly into the renal arterial blood stream. Their peculiarity lies in the fact that renin is not itself a hormone but is an enzyme that catalyzes the formation of the active hormones, the angiotensins. Renin and the other components of the renin-angiotensin system are also found at various extrarenal sites, including the brain. Renin, which is a protease with high substrate specificity, is both the initiating and the rate-limiting element in the production of the active peptide hormones. It releases the decapeptide angiotensin I by cleaving the peptide bond between residues #10 and #11 of its substrate, angiotensinogen. Angiotensinogens are glycoproteins, present in abundance in the plasma globulin fraction and synthesized by the liver. After renin acts on its substrate, angiotensinogen, to produce angiotensin I, angiotensin converting enzyme (ACE; Kininase II; Dipeptidyl Carboxypeptidase) catalyzes the conversion of angiotensin I into angiotensin II which is the classic vasoconstrictor agent with its powerful pressor effect.

U.S. Pat. No. 3,706,728 discloses that N(6)-alkyl-adenosine derivatives produce peripheral blood vessel dilating actions. It has been further taught that N(6)-[2-hydroxy-3-(1-naphthyloxy)propyl]-adenosine (I) binds to the adenosine A1 receptor in the granular juxtaglomerular cells of the kidney to inhibit release of renin into the plasma, ultimately resulting in a reduction in circulating angiotensin II, thus reducing arterial blood pressure and heart rate in hypertensive models (Federation Proceedings 44:879 & 1643, 1985). Thus, this compound has an excellent profile for the treatment of hypertension and congestive heart failure and may also be useful in the treatment of angina.

One of the disadvantages of other adenosine analogs is that they produce sedation and generalized central nervous system depression. Thus, there is a need in this art for a renin inhibiting compound which has a decreased incidence of such side effects. It is an object of the present invention to produce a compound which will effectively inhibit the production of renin, and which will display a lowered incidence of the side effects of sedation and central nervous system depression.

SUMMARY OF THE INVENTION

Compound I is represented by the formula:

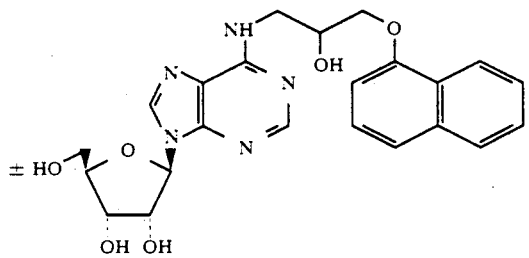

This compound is disclosed in U.S. Pat. No. 4,388,308. The '308 patent did not characterize this compound as a racemate or teach that there were desirable isomeric forms. In the present invention, compound I was subsequently resolved into two isomeric forms at the number two carbon of the propyl moiety. The S diastereomer was found in this invention to display a different solubility and melting point. Further investigation revealed that although it has a similar pharmacologic profile, the S diastereomer (II):

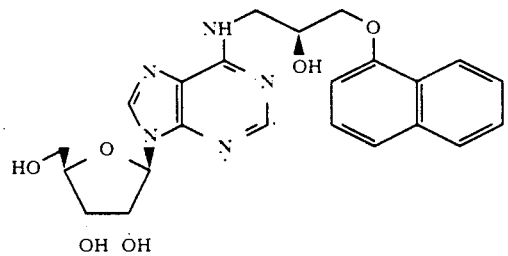

has less central nervous system toxicity than the racemic mixture. This property of the S diastereomer is unexpected because the diastereomers and the racemic mixture thereof appear to be otherwise identical pharmacologically. The isolation or chiral synthesis of the S diastereomer of compound I produces a compound useful in the treatment of hypertension, congestive heart failure and angina. The invention further provides dosage unit forms adapted for oral and parenteral administration. Also provided for in this invention are the pharmaceutically acceptable salts of the diastereomer.

DETAILED DESCRIPTION OF THE INVENTION

As used herein the expression "hypertension" is defined as a persistently high arterial blood pressure which may have either no known underlying cause (primary, idiopathic or essential hypertension) or which may have a known cause (secondary hypertension) due to or associated with a variety of primary diseases, such as renal disorders, disorders of the central nervous system, endocrine diseases and vascular diseases.

The term "congestive heart failure" is defined to mean a syndrome in a mammal due to heart disease and characterized by breathlessness and abnormal sodium and water retention, resulting in edema and congestion, which congestion may occur in the lungs or the peripheral circulation, or in both, depending on whether the heart failure is right-sided, left-sided or general.

The term "angina" is defined as spasmodic, choking, or suffocative pain, and especially as denoting angina pectoris which is a paroxysmal thoracic pain due, most often, to anoxia of the myocardium.

The term "pharmaceutically acceptable salts" refers to non-toxic salts of the compounds of this invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate, clavulanate and the like salts.

The most especially preferred compound representative of the invention is the compound namely $N^6$-[2S-hydroxy-3-(1naphthalenyloxy)propyl]-adenosine, and the pharmaceutically acceptable salts thereof, and which is of the formula:

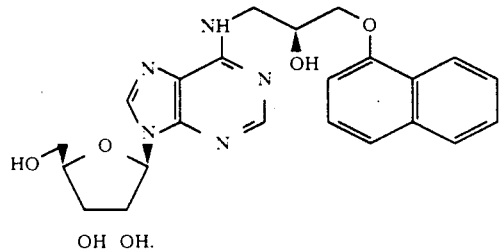

Compounds of the invention can be prepared readily according to the following reaction scheme or modifications thereof using readily available starting materials, reagents and conventional synthesis procedures. In these reactions, it is also possible to make use of variants which are in themselves known, but are not mentioned here in greater detail.

Scheme 1

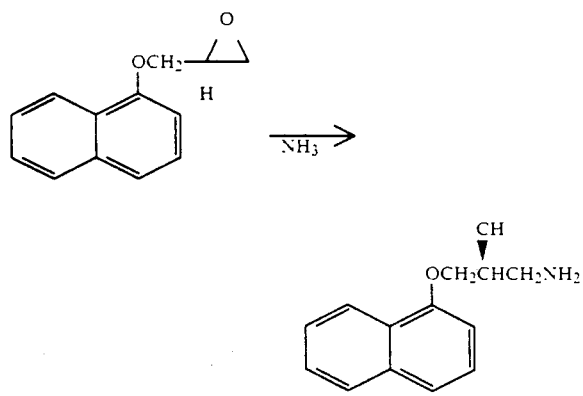

-continued
Scheme 1

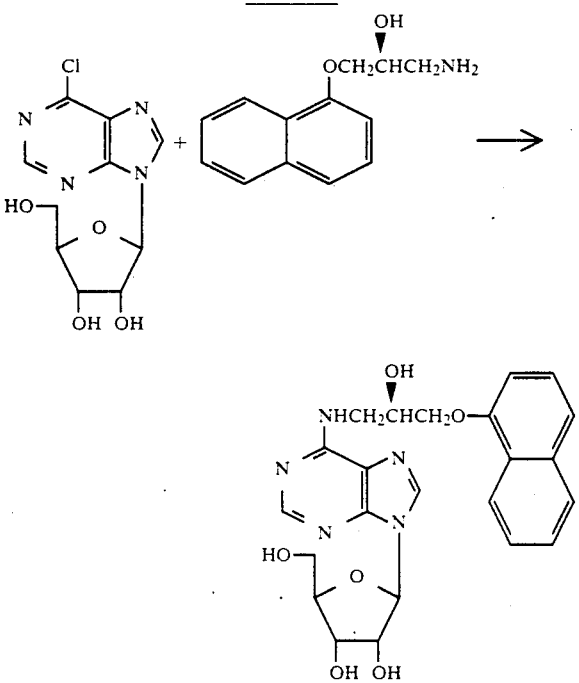

The compound of the present invention can be administered in such oral dosage forms as tablets, capsules, pills, powders, granules, elixirs, tinctures, suspensions, syrups, emulsions and suspensions. Likewise, it may also be administered in intravenous, intraperitoneal, subcutaneous or intramuscular form, all using forms known to those of ordinary skill in the pharmaceutical arts. In general, the preferred form of administration is oral. An effective but non-toxic amount of the compound is employed in the treatment of hypertension, angina or congestive heart failure. The dosage regimen utilizing the compound of the present invention is selected in accordance with a variety of factors including the type, species, age, weight, sex and medical condition of the patients; with the severity of the condition to be treated, the route of administration, the renal and hepatic function of the patient, the route of administration and the particular compound employed or salt thereof. An ordinarily skilled veterinarian or physician can readily determine and prescribe the effective amount of the drug required to prevent, treat or arrest the progress of the condition.

Oral dosages of the compound in the present invention, when used for the indicated cardiovascular effects, will range between about 0.1 mg/kg/day to about 1000 mg/kg/day and preferably 1.0 to 100 mg/kg/day. Advantageously, the compound of the present invention may be administered in a single daily dose or the total daily dosage may be administered in divided doses of 2, 3 or 4 times daily.

In the pharmaceutical compositions and methods of the present invention, the foregoing compounds described in detail above will form the active ingredients and will typically be administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of tablets or capsules, the active drug component may be combined with an oral non-toxic pharmaceutically acceptable inert carrier such as lactose, starch, sucrose, glucose, methylcellulose, magnesium stearate, dicalcium phosphate, calcium sulfate, mannitol, sorbitol and the like; for oral administration in liquid form, the active drug components may be combined with any oral non-toxic pharmaceutically acceptable inert carrier such as ethanol, glycerol, water, and the like. Moreover, when desired or necessary, suitable binders, lubricants, disintegrating agents and coloring agents can also be incorporated in the mixture. Suitable binders include starch, gelatin, natural sugars such as glucose or beta-lactose, corn sweeteners, natural and synthetic gum such as acacia, tragacanth or sodium alginate, carboxymethylcellulose, polyethylene glycol and waxes. Lubricants for use in these dosage forms include boric acid, sodium benzoate, sodium acetate, sodium chloride and the like. Disintegrators include, without limitation, starch, methylcellulose, agar, bentonite, xanthan gum and the like.

The compound of this invention may also be administered by intravenous route in doses ranging from 0.01 to 10 mg/kg/day.

The compound of this invention exhibits renin-release inhibiting activity useful in the treatment of hypertension, congestive heart failure and angina. The test procedures employed to measure this activity of the compounds of the present invention are described below.

The effects of compounds I and II were tested intravenously or intragastrically in conscious spontaneously hypertensive rats (SHR). The rats were anesthetized with ether and the left carotid artery and right jugular vein were cannulated with polyethylene tubing. The rats were allowed three to five hours recovery from anesthesia for the I.V. studies and 12 to 18 hours for the oral studies. Mean arterial pressure (MAP, in mm/Hg) and heart rate (HR, beats/min.) were measured from the artery; intravenous administration of compounds was performed by injection into the vein. Oral administration was performed by gastric intubation. Compounds were dissolved in DMSO for I.V. studies and injected in volumes of 100 $\mu$l/kg or less (N=5 per pound). Doses were 3 to 1,000 $\mu$g/kg. Compounds were dissolved in polyethylene glycol for oral administration and injected in volumes of 1 ml/kg at a dose of 20 mg/kg/day for three days (N=3 to 6 per compound).

The resting MAP and HR for the SHR ranged between 160-200 mm Hg and 330/350 b/min., respectively. The effects of the compounds on MAP and HR are shown in Table I.

required to decrease HR by 100 b/min. ranged between 31 and 37 $\mu$g/kg and also were not significantly different among the compounds. Table I also shows the effects of the compounds on day 2 of oral administration which are representative of the results from 3 days of testing. All three compounds lowered MAP and HR to the same extent with a similar duration of action after oral administration. Thus, the effects of the three compounds on MAP and HR were indistinguishable both by I.V. and oral administration.

The inhibition of the release of renin reduces the amount of circulating renin and the activity of plasma renin. The reduction in plasma renin activity (PRA) is associated with a reduction in circulating angiotensin II. Angiotensin II is a potent vasoconstrictor and is responsible for elevated vascular resistance and high blood pressure in hypertension. Inhibition of renin release is, therefore, expected to be useful in the treatment of hypertension by reducing the amount of circulating angiotensin II. Likewise, inhibition of renin release may be expected to be useful in the treatment of angina and congestive heart failure by inducing vasodilation to reduce the afterload of the myocardium. Also, inhibition of renin release may further be expected to be useful in the treatment of angina, since indirectly inhibiting the formation of angiotensin will prevent angiotensin's direct action on the membrane of atrial and ventricular muscle (angiotensin prolongs the plateau phase of the action potential, increasing inward calcium current and force of contraction thus increasing the work of the heart.) Furthermore, inhibition of renin may be expected to be useful in congestive heart failure, since the essential hypertension caused by elevated renin levels is itself one of the causes of the decreased cardiac output that initiates the vicious cycle of the congestive heart failure syndrome.

The present invention inhibits the release of renin by activation of adenosine Al receptors in the granular juxtaglomerular cells of the kidney. The binding potency of compounds I and II to the adenosine Al receptor was measured according to the method of Schwabe, U. et al., Naunyn Schmeid. Arch. Pharmacol. 321:84, 1982. Crude plasma membranes were prepared and varying concentrations of compounds I or II were added to the membrane preparation in the presence of $^{125}$I-N-p-hydroxyphenylisopropyladenosine (HPIA). The affinity of the compounds for the adenosine Al receptor was estimated from the concentrations necessary to inhibit the binding of HPIA by 50% (IC50). The results of these studies are shown in Table II.

TABLE I

| | Effects of compounds I and II on MAP and HR in SHR | | | |
|---|---|---|---|---|
| | IV DOSE ($\mu$g/kg) TO | | MAXIMUM DECREASE AT 20 MG/KG ig | |
| COMPOUND | DECREASE MAP by 40 mmHg | DECREASE HR by 100 b/min | MAP (mmHg) | HR (b/min) |
| I | 52 ± 1.3 | 37 ± 1.3 | 50 ± 13 | 214 ± 14 |
| II | 47 ± 1.2 | 36 ± 1.2 | 62 ± 7 | 202 ± 24 |

MAP = mean arterial pressure;
HR = heart rate;
SHR = spontaneously hypertensive rat The intravenous doses required to decrease MAP by 40 mm Hg ranged between 33 and 52 $\mu$g/kg and were not significantly different among the compounds. The doses

TABLE II

BINDING POTENCY (IC50) OF COMPOUNDS I AND II
FOR THE ADENOSINE A1 RECEPTOR

| COMPOUND | IC50 ($10^{-9}$M) |
|---|---|
| I | 1.2 |
| II | 1.2 |

The IC50's of the compounds were identical, indicating that they all had the same relative affinity for the adenosine A1 receptor.

Adenosine A1 receptor stimulation will inhibit the release of renin from the kidney. A stimulus for the release of renin is renal ischemia. The ability of the compounds of the present invention to prevent an increase in PRA following renal ischemia was tested in rats with both renal arteries ligated. Sprague-Dawley rats were anesthetized with ether and the renal arteries were ligated. Three to five hours after anesthesia, arterial blood was sampled and compounds I and II were administered in polyethylene glycol at 1 mg/kg I.V. At 30 and 60 minutes after administration, arterial blood was sampled for PRA measurement by the method of Sealy, J. E. et al., Cardiovasc. Med. 2:1079, 1977. The results are presented in Table III.

TABLE III

EFFECTS OF COMPOUNDS I AND II ON PRA
AT 30 AND 60 MINUTES AFTER DOSING
IN THE BILATERAL RENAL ARTERY LIGATED RAT
CHANGE IN PRA (ngAI/ml/hr)

| COMPOUND | 30 minutes | 60 minutes |
|---|---|---|
| VEHICLE | 4.5 ± 1.1* | 12 ± 2.7* |
| I | −2.9 ± 5.0 | −9.4 ± 7.4⁻ |
| II | −11.7 ± 3.5⁻,*,# | −13.8 ± 4.9⁻,* |

* = different from zero, $p < .05$;
⁻ = different from vehicle, $p < .05$;
# = different from I, $p < .05$.

With vehicle treatment there were increases in PRA above pre-treatment levels at 30 and 60 minutes. These increases were prevented to the same extent by compounds I and II. Thus, these compounds appeared equieffective in inhibiting the release of renin.

Adenosine analogs tend to produce sedation and central nervous system depression which have prevented their therapeutic utility. The compounds of the invention, at doses which lower arterial pressure in the SHR, show no evidence of CNS depression. The ataxia produced by compounds of the present invention was measured in mice by injecting the compounds IP at doses of 32, 56, or 75 mg/kg in an aqueous suspension, n=7 per dose. The mice had previously been trained to remain on a rotating rod. After dosing, the percent of mice unable to remain on the rotating rod was determined. Analysis of the results indicated that there were not significant differences among the three doses used, so the results were pooled for the three doses (average=54±12 mg/kg). The mice were also observed at various time intervals for behavioral signs of toxicity.

Table IV shows the results of the rotating rod studies. Compound II produced less ataxia at 0.5 or 3 hours as compared to compound I.

TABLE IV

ATAXIC EFFECTS OF COMPOUNDS I AND II
(54 ± 12 mg/kg ip) IN MICE

| | PERCENT ATAXIC | |
|---|---|---|
| COMPOUND | 0.5 HOUR | 3 HOUR |
| I | 33 ± 10 | 95 ± 5 |
| II | 14 ± 8* | 48 ± 21* |

* = Significantly different from compound I. $p < .05$

Thus, compound II produced less motor toxicity than compound I. Table V shows the results on behavioral changes at 75 mg/kg at various times after administration.

TABLE V

BEHAVORIAL TOXICITY AT VARIOUS TIMES AFTER 75 MG/KG IP IN MICE

| TIME (HR) | MOTOR DEPRESSION | PTOSIS | RESPIRATORY DEPRESSION | FLACCIDITY | LOSS OF RIGHTING REFLEX |
|---|---|---|---|---|---|
| CMPD I | | | | | |
| 0.5 | + | + | + | | |
| 3 | + | + | + | + | + |
| 18-20 | + | − | + | +* | |
| 24 | | | | | |
| CMPD II | | | | | |
| 0.5 | + | + | + | | |
| 3 | + | + | + | | |
| 18-20 | + | + | + | + | |
| 24 | −# | −# | −# | | |

− = toxic symptom observed;
* = 2/7;
= 5/7

Both compounds produced similar toxicity at 0.5 hours, which included motor depression, ptosis, and respiratory depression. At 3 hours, compound I also produced flaccidity and loss of righting reflex.

The results of the biological testing demonstrate that compounds I and II have similar pharmacologic profiles but that compound II is unexpectedly less CNS toxic than compound I, especially with regard to ataxia. Thus, compound II may be administered to mammals for the treatment of hypertension and other cardiovascular diseases such as congestive heart failure and angina pectoris in doses that produce less central nervous system toxicity than compound I.

The following non-limiting examples further illustrate details for the preparation of the compound of the present invention. Those skilled in the art will readily understand that known variations of the conditions and processes of the following preparative procedures can be used to prepare these compounds. All temperatures are degrees Celsius unless otherwise noted. Melting points were determined on a Thomas-Hoover Unimelt capillary apparatus and are not corrected. Unless otherwise noted, I.R. and NMR spectra, were consistent with the assigned structure.

EXAMPLE I

Compound I was synthesized from a mixture of 6-chloropurine riboside and a d,l mixture of 1(3-amino-2-hydroxy-1-propyloxy)-napthalene as described in U.S. Pat. No. 4,388,308, and set forth as follows. 20 g (0.0698 moles) of 6-chloropurine 18.4 g (0.0847 moles) of (1-naphthalenyloxy) 2-hydroxy-propylamine, 20 ml of triethylamine and 600 ml of anhydrous methanol were heated under $N_2$ at reflux for 16 hours. Solvent was distilled off under vacuum. The resulting residue was stirred two days with 1:1 methylene chloride-water. This mixture was filtered and the solid was crystallized twice from methanol. The solvated resultant product was dried under high vacuum, heating at a temperature just under its melting point, and raising that temperature as the melting point raised, until all of the solvate was gone.

The S diastereomer and R diastereomer were separated using a chiral HPLC analytical column, each in greater than 99% purity. The S isomer was less soluble in MeOH and had a melting point of 148-150 degrees. The R isomer was more soluble in MeOH and had a melting point of 163-164 degrees.

EXAMPLE II

An alternative synthesis was devised to produce the pure S isomer. 2.69 g (0.0174 moles) of 6-chloropurine 3.79 g (0.0174 moles) of S-(1-naphthalenyloxy) 2-hydroxypropylamine, 3.52 g (0.0348 moles) of triethylamine and 100 ml of anhydrous methanol were heated under at reflux for 16 hours. Solvent was distilled off under vacuum. The resulting residue wa stirred overnight with 1:1 methylene chloride-water. The mixture was filtered and the solid residue was crystallized twice from methanol and after drying at 80°/1 mm. furnished white prisms, m.p. 148-150° having greater than 99% diastereomeric purity. Additional crops could be obtained from the mother liquor.

Analysis: Calculated for $C_{23}H_{25}N_5O_6$;
C, 59.09: H, 5.37; N, 14.98.
Found: C, 58.74; H, 5.47; N, 14.57.

While the invention has been described and illustrated with reference to certain prepared embodiments thereof, those skilled in the art will appreciate that various changes, modifications and substitutions can be made therein without departing from the spirit and scope of the invention. For example, effective dosages other than the preferred range as set forth herein above may be applicable as a consequence of variations in the responsiveness of the mammal being treated for severity of hypertension, angina or congestive heart failure, dosage related adverse effects, if any, and analogous considerations. Likewise, the specific pharmacological responses observed may vary according to and depending upon the particular active compound selected or whether there are present certain pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow, and that such claims be interpreted as broadly as is reasonable.

What is claimed is:

1. A compound, namely N6-[2S-hydroxy-3-(1-naphthalenyloxy)propyl]adenosine and the pharmaceutically acceptable salts thereof, and which is of the structural formula

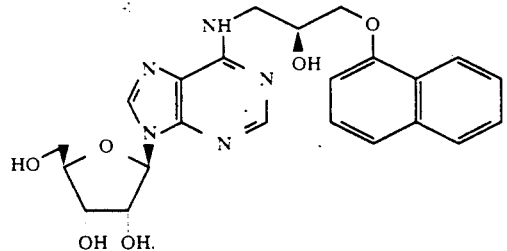

2. A pharmaceutical composition comprised of a pharmaceutically acceptable non-toxic carrier in combination with a compound according to claim 1.

3. A method of decreasing plasma renin activity in a mammal in need of such regulation, comprising administering to said mammal a pharmacologically effective amount of a compound as claimed in claim 1.

4. A method of treating hypertension in a mammal in need of such treatment, comprising administering to said mammal a pharmacologically effective amount of a compound as claimed in claim 1.

5. A method of treating congestive heart failure in a mammal in need of such treatment, comprising administering to said mammal a pharmacologically effective amount of a compound as claimed in claim 1.

6. A method of treating angina in a mammal in need of such treatment, comprising administering to said mammal a pharmacologically effective amount of a compound as claimed in claim 1.

* * * * *

UNITED STATES PATENT AND TRADEMARK OFFICE
CERTIFICATE OF CORRECTION

PATENT NO. : 5,032,584

DATED : Jul. 16, 1991

INVENTOR(S) : Lowrie et al.

It is certified that error appears in the above-identified patent and that said Letters Patent is hereby corrected as shown below:

Column 2, lines 11-20, the structure reading, "

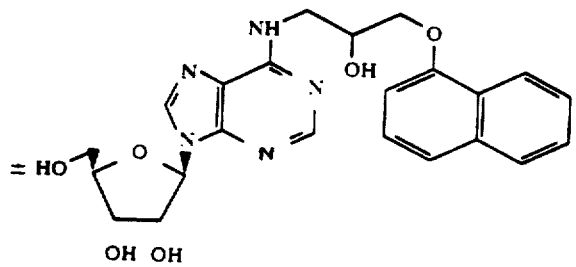

Should read --

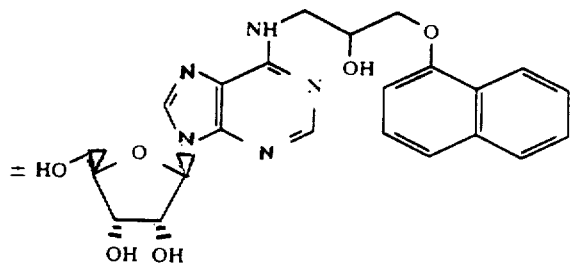

--.

UNITED STATES PATENT AND TRADEMARK OFFICE
CERTIFICATE OF CORRECTION

PATENT NO. : 5,032,584

DATED : Jul. 16, 1991

INVENTOR(S) : Lowrie et al.

It is certified that error appears in the above-identified patent and that said Letters Patent is hereby corrected as shown below:

Column 2, lines 34-43, the structure reading, "

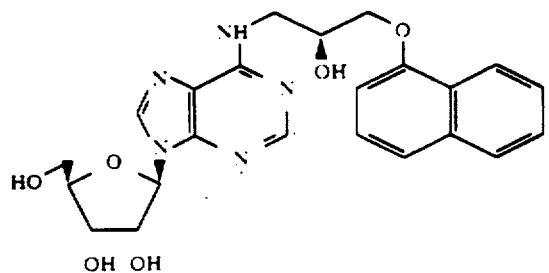

Should read --

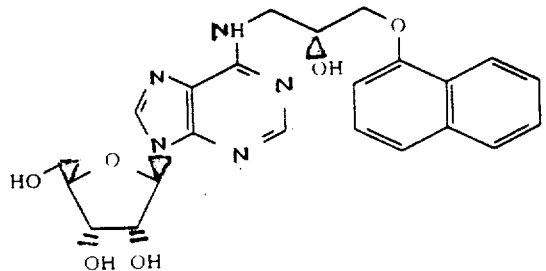

--.

UNITED STATES PATENT AND TRADEMARK OFFICE
CERTIFICATE OF CORRECTION

PATENT NO. : 5,032,584

DATED : Jul. 16, 1991

INVENTOR(S) : Lowrie et al.

It is certified that error appears in the above-identified patent and that said Letters Patent is hereby corrected as shown below:

Column 3, lines 30-38, the structure reading "

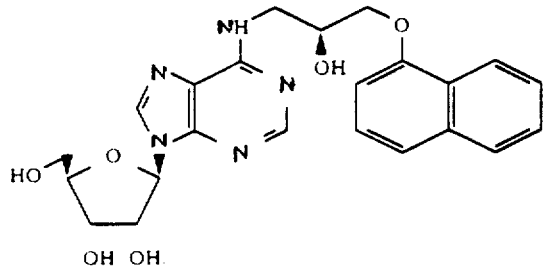

Should read --

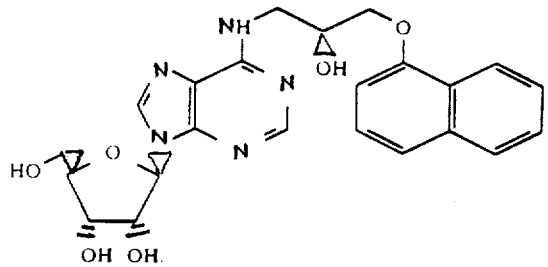

--.

UNITED STATES PATENT AND TRADEMARK OFFICE
CERTIFICATE OF CORRECTION

PATENT NO. : 5,032,584

DATED : Jul. 16, 1991

INVENTOR(S) : Lowrie et al.

It is certified that error appears in the above-identified patent and that said Letters Patent is hereby corrected as shown below:

Column 3, line 55, the structure reading "

Column 9, line 33, reading "The resulting residue wa stirred" should read -- The resulting residue was stirred --.

Column 10, line 16, reading "namely N6-[2S-hydroxy-" should read -- namely $N^6$-[2S-hydroxy- --.

UNITED STATES PATENT AND TRADEMARK OFFICE
CERTIFICATE OF CORRECTION

PATENT NO.  : 5,032,584

DATED       : Jul. 16, 1991

INVENTOR(S) : Lowrie et al.

It is certified that error appears in the above-identified patent and that said Letters Patent is hereby corrected as shown below:

Column 10, lines 21-30, the structure reading "

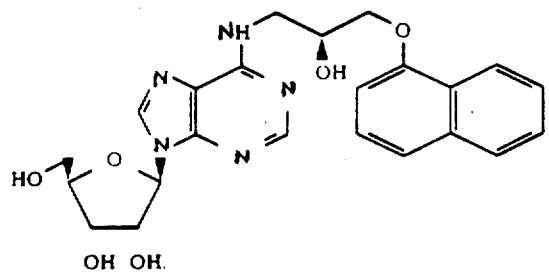  Should read -- 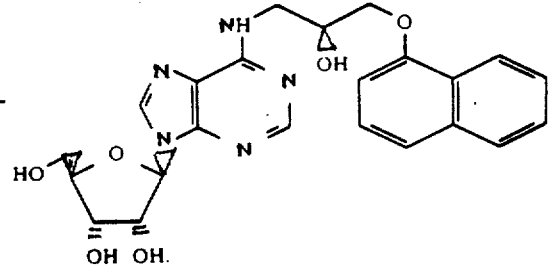

Signed and Sealed this

Eleventh Day of May, 1993

Attest:

MICHAEL K. KIRK

Attesting Officer

Acting Commissioner of Patents and Trademarks